(12) United States Patent
Abe

(10) Patent No.: US 8,383,274 B2
(45) Date of Patent: Feb. 26, 2013

(54) NONAQUEOUS ELECTROLYTE SOLUTION FOR LITHIUM BATTERY, LITHIUM BATTERY USING SAME, AND FORMYLOXY GROUP-CONTAINING COMPOUND USED THEREIN

(75) Inventor: Koji Abe, Yamaguchi (JP)

(73) Assignee: Ube Industries, Ltd., Ube-Shi (JP)

( * ) Notice: Subject to any disclaimer, the term of this patent is extended or adjusted under 35 U.S.C. 154(b) by 25 days.

(21) Appl. No.: 13/003,920

(22) PCT Filed: Jul. 1, 2009

(86) PCT No.: PCT/JP2009/062039
§ 371 (c)(1),
(2), (4) Date: Apr. 14, 2011

(87) PCT Pub. No.: WO2010/007889
PCT Pub. Date: Jan. 21, 2010

(65) Prior Publication Data
US 2011/0183199 A1   Jul. 28, 2011

(30) Foreign Application Priority Data

Jul. 15, 2008  (JP) ............................... 2008-183280
Apr. 9, 2009  (JP) ............................... 2009-095077

(51) Int. Cl.
*H01M 6/16* (2006.01)
(52) U.S. Cl. ........................ 429/324; 429/188; 558/52
(58) Field of Classification Search .............. 429/334
See application file for complete search history.

(56) References Cited

U.S. PATENT DOCUMENTS

| | | | |
|---|---|---|---|
| 6,130,354 A | 10/2000 | Mair | |
| 2007/0231707 A1* | 10/2007 | Abe et al. | 429/340 |
| 2009/0053598 A1 | 2/2009 | Abe et al. | |
| 2010/0291437 A1 | 11/2010 | Abe et al. | |

FOREIGN PATENT DOCUMENTS

| | | |
|---|---|---|
| JP | 2000-26365 | 1/2000 |
| JP | 2002-110234 | 4/2002 |
| JP | 2002110234 A * | 4/2002 |
| JP | 2006-278106 | 10/2006 |
| WO | WO 2005/117197 A1 | 12/2005 |
| WO | WO 2006/077763 A1 | 7/2006 |

OTHER PUBLICATIONS

International Search Report issued Oct. 6, 2009 in PCT/JP2009/062039 (with English Translation of Category of Cited Documents).

* cited by examiner

*Primary Examiner* — Ula C Ruddock
*Assistant Examiner* — Scott J Chmielecki
(74) *Attorney, Agent, or Firm* — Oblon, Spivak, McClelland, Maier & Neustadt, L.L.P.

(57) ABSTRACT

Disclosed are a nonaqueous electrolytic solution for lithium secondary battery comprising an electrolyte dissolved in a nonaqueous solvent and containing at least one compound represented by the formula (I) in an amount of from 0.01 to 10% by mass of the nonaqueous electrolytic solution; a lithium battery containing the electrolytic solution and excellent in low-temperature and high-temperature cycle property; and a formyloxy group-containing compound having a specific structure which is used in lithium batteries, etc.

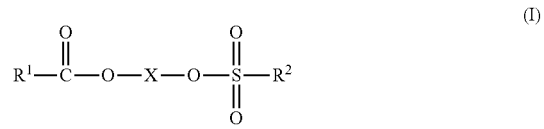

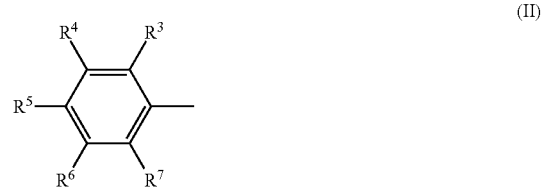

(wherein X represents an alkylene group, an alkenylene group or an alkynylene group; $R^1$ represents H, an alkyl group, a cycloalkyl group or a group of the formula (II); $R^2$ represents an alkyl group, a cycloalkyl group or a group of the formula (II); $R^3$ to $R^7$ each represent H, F, a methoxy group or an ethoxy group.)

14 Claims, No Drawings

NONAQUEOUS ELECTROLYTE SOLUTION FOR LITHIUM BATTERY, LITHIUM BATTERY USING SAME, AND FORMYLOXY GROUP-CONTAINING COMPOUND USED THEREIN

TECHNICAL FIELD

The present invention relates to a nonaqueous electrolytic solution for lithium battery, a lithium battery using the same, and a novel formyloxy group-containing compound usable for lithium batteries, etc.

BACKGROUND ART

In recent years, lithium secondary batteries have been widely used as power supplies for small-size electronic devices such as mobile telephones, notebook-size personal computers and the like, and for electric vehicles as well as for electric power storage, etc. These electronic devices and vehicles may be used in a broad temperature range, for example, at midsummer high temperatures or at frigid low temperatures, and are therefore required to have a well-balanced cycle property in a wide temperature range.

A lithium secondary battery is mainly constituted of a positive electrode and a negative electrode containing a material capable of absorbing and releasing lithium, and a nonaqueous electrolytic solution containing a lithium salt and a nonaqueous solvent. As the nonaqueous solvent, used are carbonates such as ethylene carbonate (EC), propylene carbonate (PC), etc.

As the negative electrode, known are metal lithium, and metal compounds (metal elemental substances, oxides, alloys with lithium, etc.) and carbon materials capable of absorbing and releasing lithium. In particular, lithium secondary batteries using a carbon material capable of absorbing and releasing lithium such as coke, artificial graphite, natural graphite or the like have been widely put into practical use.

For example, it is known that, in the lithium secondary battery using a highly-crystalline carbon material such as artificial graphite, natural graphite or the like as the negative electrode material, the decomposed product or gas generated through reductive decomposition of the solvent in the nonaqueous electrolytic solution on the surface of the negative electrode during charging detracts from the electrochemical reaction favorable for the battery, therefore worsening the cycle property of the battery. Deposition of the decomposed product of the nonaqueous solvent interferes with smooth absorption and release of lithium by the negative electrode, and therefore, in particular, the cycle property at low temperatures and at high temperatures may be thereby often worsened.

In addition, it is known that a lithium secondary battery using a lithium metal or its alloy, or a metal elemental substance such as tin, silicon or the like or its metal oxide as the negative electrode material may have a high initial battery capacity but its battery performance such as battery capacity and cycle property greatly worsens, since the micronized powdering of the material is promoted during cycles thereby bringing about accelerated reductive decomposition of the nonaqueous solvent, as compared with the negative electrode of a carbon material. In addition, the micronized powdering of the negative electrode material and the deposition of the decomposed product of the nonaqueous solvent may interfere with smooth absorption and release of lithium by the negative electrode, and therefore, in particular, the cycle property at low temperatures and high temperatures may be thereby often worsened.

On the other hand, it is known that, in a lithium secondary battery using, for example, $LiCoO_2$, $LiMn_2O_4$, $LiNiO_2$ or $LiFePO_4$ as the positive electrode, when the nonaqueous solvent in the nonaqueous electrolytic solution is heated at a high temperature in the charged state, the decomposed product or gas thereby locally generated through partial oxidative decomposition in the interface between the positive electrode material and the nonaqueous electrolytic solution interferes with the electrochemical reaction favorable for the battery, and therefore the battery performance such as cycle property is thereby also worsened.

As in the above, the decomposed product or gas generated through decomposition of the nonaqueous electrolytic solution on the positive electrode or the negative electrode interferes with the movement of lithium ions or swells the battery, and the battery performance is thereby worsened. Despite the situation, electronic appliances equipped with lithium secondary batteries therein are offering more and more an increasing range of functions and are being in a stream of further increase in the power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of the nonaqueous electrolytic solution may worsen the battery performance at low temperatures and high temperatures.

As a lithium primary battery, for example, there is known a lithium primary battery comprising manganese dioxide or graphite fluoride as the positive electrode and a lithium metal as the negative electrode, and this is widely used as having a high energy density. It is desired to inhibit the increase in the internal resistance of the battery during long-term storage and to improve the long-term storage property at high temperatures thereof.

Recently, further, as a novel power source for electric vehicles or hybrid electric vehicles, electric storage devices have been developed, for example, an electric double layer capacitor using activated carbon or the like as the electrode from the viewpoint of the output density thereof, and a so-called hybrid capacitor comprising a combination of the electric storage principle of a lithium ion secondary battery and that of an electric double layer capacitor (an asymmetric capacitor where both the capacity by lithium absorption and release and the electric double layer capacity are utilized) from the viewpoint of both the energy density and the output density thereof; and it is desired to improve the battery performance such as the cycle property and the high-temperature storability at high temperatures of these capacitors.

Patent Reference 1 discloses the possibility of improving the cycle property at 20° C. and 60° C. of a lithium ion secondary battery in which 2-butyne-1,4-diol diacetate is added to the nonaqueous electrolytic solution in an amount of 1% by volume therein. Patent Reference 2 discloses the possibility of improving the cycle property of a lithium ion secondary battery in which ethylene glycol dimethanesulfonate is added to the electrolytic solution in an amount of 1% by mass therein. Further, Patent Reference 3 discloses the possibility of improving the cycle property at 20° C. of a lithium ion secondary battery in which 2-butyne-1,4-diol dimethanesulfonate is added to the electrolytic solution in an amount of 1% by weight therein.

[Patent Reference 1] JP-A 2001-256995
[Patent Reference 2] JP-A 2007-095380
[Patent Reference 3] JP-A 2000-195545

DISCLOSURE OF THE INVENTION

Problems that the Invention is to Solve

An object of the present invention is to provide a nonaqueous electrolytic solution for lithium battery capable of improving the low-temperature and high-temperature cycle property thereof, a lithium battery using the same, and a novel formyloxy group-containing compound usable for lithium batteries, etc.

Means for Solving the Problems

The present inventors have investigated in detail the performance of the nonaqueous electrolytic solutions in the prior art mentioned above. As a result, the current condition is that the nonaqueous electrolytic solution in Patent Reference 1 and others could not realize a good cycle property in a wide range of low temperatures and high temperatures.

Accordingly, the present inventors have assiduously studied for the purpose of solving the above-mentioned problems and have found that, when a compound having two and different substituents of a specific acyloxy group (—OCOR) and a specific sulfonyloxy group (—OSO$_2$R) bonded via a hydrocarbon group is added to the nonaqueous electrolytic solution, then the low-temperature and high-temperature cycle property can be improved, and have reached the present invention.

Specifically, the present invention provides the following (1) to (3):

(1) A nonaqueous electrolytic solution for lithium battery comprising an electrolyte dissolved in a nonaqueous solvent, which comprises at least one compound represented by the following general formula (I) in an amount of from 0.01 to 10% by mass of the nonaqueous electrolytic solution:

[Formula 1]

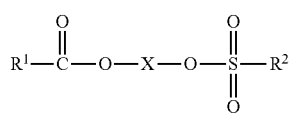

(I)

(wherein X represents an alkylene group having from 1 to 6 carbon atoms, an alkenylene group having from 4 to 8 carbon atoms, or an alkynylene group having from 4 to 8 carbon atoms; R$^1$ represents a hydrogen atom, an alkyl group having from 1 to 6 carbon atoms, a cycloalkyl group having from 3 to 8 carbon atoms, or a group represented by the following general formula (II); R$^2$ represents an alkyl group having from 1 to 6 carbon atoms, a cycloalkyl group having from 3 to 8 carbon atoms, or a group represented by the following general formula (II); provided that at least one hydrogen atom of the alkyl group may be substituted with a halogen atom.)

[Formula 2]

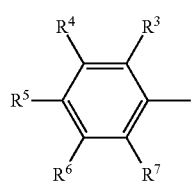

(II)

(wherein R$^3$ to R$^7$ each independently represent any of a hydrogen atom, a fluorine atom, a methoxy group, or an ethoxy group.)

(2) A lithium secondary battery comprising a positive electrode, a negative electrode and a nonaqueous electrolytic solution of an electrolyte salt dissolved in a nonaqueous solvent, wherein the nonaqueous electrolytic solution at least one compound represented by the above-mentioned general formula (I) in an amount of from 0.01 to 10% by mass of the nonaqueous electrolytic solution.

(3) A formyloxy group-containing compound represented by the following general formula (III):

[Formula 3]

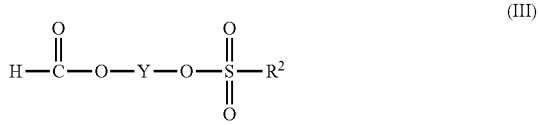

(III)

(wherein Y represents an alkenylene group having from 4 to 8 carbon atoms, or an alkynylene group having from 4 to 8 carbon atoms; and R$^2$ has the same meaning as above.)

Advantage of the Invention

According to the present invention, there are provided a nonaqueous electrolytic solution for lithium battery capable of improving the low-temperature and high-temperature cycle property thereof, a lithium battery using the same, and a novel formyloxy group-containing compound usable in lithium batteries, etc.

BEST MODE FOR CARRYING OUT THE INVENTION

Nonaqueous Electrolytic Solution

The nonaqueous electrolytic solution for lithium battery of the present invention is a nonaqueous electrolytic solution of an electrolyte dissolved in a nonaqueous solvent, and is characterized by containing at least one compound represented by the following general formula (I) in an amount of from 0.01 to 10% by mass of the nonaqueous electrolytic solution.

[Formula 4]

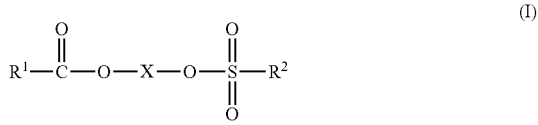

(I)

Though not clear, the reason why the nonaqueous electrolytic solution of the present invention can improve the low-temperature and high-temperature cycle property thereof may be considered as follows: Specifically, the compound represented by the general formula (I) of the present invention has two and different substituents of a specific acyloxy group (—OCOR$^1$) and a specific sulfonyloxy group (—OSO$_2$R$^2$) bonded via a hydrocarbon group X, and therefore has a reduction potential quite different from that of a compound having two but the same substituents. Regarding this, it may be considered that, when a mixed surface film derived from the two and different substituents is formed on an electrode, a good mixed surface film could be formed thereon owing to the reduction potential that could not be anticipated in the case where a compound having two and the same substituents, such as 2-butyne-1,4-diol diacetate described in Patent Reference 1, is used, and therefore the effect of specifically improving the low-temperature and high-temperature cycle property could be expressed.

In particular, it has been found that the compound where the acyloxy group is a formyloxy group (—OCOH) and the hydrocarbon chain that bonds the substituents contains a multiple bond can form an especially good mixed surface film and can enhance the effect of improving the low-temperature and high-temperature cycle property. This may be because, when the hydrocarbon chain that bonds the formyloxy group (—OCOH) and the sulfonyloxy group (—OSO$_2$R$^2$) contains a multiple bond, then the two substituents may be more readily decomposed than in a case having any other acyloxy group than the formyloxy group and therefore a polymer surface film having the conjugated bond derived from the multiple bond may be formed more readily and the electron conductivity of the surface film may be thereby enhanced.

In the above-mentioned general formula (I), X represents a linear or branched alkylene group having from 1 to 6 carbon atoms, an alkylene group having a substituent, a linear or branched alkenylene group having from 4 to 8 carbon atoms, or a linear or branched alkynylene group having from 4 to 8 carbon atoms; R$^1$ represents a hydrogen atom, a linear or branched alkyl group having from 1 to 6 carbon atoms, a cycloalkyl group having from 3 to 8 carbon atoms, or a group represented by the following general formula (II); R$^2$ represents a linear or branched alkyl group having from 1 to 6 carbon atoms, a cycloalkyl group having from 3 to 8 carbon atoms, or a group represented by the following general formula (II); provided that at least one hydrogen atom of the alkyl group may be substituted with a halogen atom.

In the above-mentioned general formula (I), the unsubstituted or substituted alkylene group for X includes an unsubstituted alkylene group such as a methylene group, an ethylene group, an ethylidene group (branched), a trimethylene group, a propane-1,2-diyl group (branched), a propylidene group (branched), a tetramethylene group, a butane-1,3-diyl group (branched), a 2-methylpropane-1,2-diyl group (branched), a butylidene group (branched), a 1,5-pentylene group, a 1,6-hexylene group, etc.; as well as a group —CH$_2$CH(OCOR$^1$)—CH$_2$—, a group —CH$_2$C(CH$_2$OCOR$^1$)—, a group —CH$_2$CH(OSO$_2$R$^2$)—CH$_2$— (in these groups, R$^1$ and R$^2$ have the same meanings as those in the general formula (I)). Modifications where the main chain of the unsubstituted or substituted alkylene group, propanediyl group is changed to a butane-diyl group or a pentane-diyl group also exhibit the same effect as that of the present invention.

The alkenylene group for X includes a 2-butenylene group, a 2-pentenylene group, a 3-hexenylene group, a 1,4-dimethyl-2-butenylene group, a 1,1,4,4-tetramethyl-2-butenylene group, etc.

The alkynylene group for X includes a 2-butynylene group, a 2-pentynylene group, a 3-hexynylene group, a 1,4-dimethyl-2-butynylene group, a 1,1,4,4-tetramethyl-2-butynylene group, etc.

Of those, from the viewpoint of improving the low-temperature and high-temperature cycle property, X is preferably an alkylene group having from 2 to 4 carbon atoms such as an ethylene group, a trimethylene group, a tetramethylene group, etc.; a 2-formyloxypropane-1,3-diyl group, a 2-methanesulfonyloxypropane-1,3-diyl group, a 3-formyloxypropane-1,2-diyl group; or an alkynylene group having from 4 to 6 carbon atoms such as a 2-butynylene group, etc.; more preferably an alkylene group such as an ethylene group, a trimethylene group, a tetramethylene group, etc.; or an alkynylene group such as a 2-butynylene group, etc.; even more preferably an ethylene group or a 2-butynylene group.

In the above-mentioned general formula (I), the alkyl group having from 1 to 6 carbon atoms for R$^1$ and R$^2$ includes a linear alkyl group such as a methyl group, an ethyl group, a 1-propyl group, a 1-butyl group, etc.; a branched alkyl group such as a 2-propyl group, a 2-butyl group, an isobutyl group, a t-butyl group, etc.; a linear alkyl group substituted with a halogen atom, such as a fluoromethyl group, a chloromethyl group, a bromomethyl group, a trifluoromethyl group, a 2,2,2-trifluoroethyl group, a pentafluoropropyl group, etc.

Of those, from the viewpoint of improving the low-temperature and high-temperature cycle property, a methyl group, an ethyl group and a trifluoromethyl group are preferred for R$^1$ and R$^2$.

In the above-mentioned general formula (I), the cycloalkyl group having from 3 to 8 carbon atoms for R$^1$ and R$^2$ includes a cyclopropyl group, a cyclobutyl group, a cyclopentyl group, a cyclohexyl group, a cycloheptyl group, a cyclooctyl group, etc. From the viewpoint of improving the low-temperature and high-temperature cycle property, preferred are a cyclopentyl group and a cyclohexyl group.

In the above-mentioned general formula (I), the group represented by the general formula (II) for R$^1$ and R$^2$ includes a phenyl group, a phenyl group substituted with only a fluorine atom, such as a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,5-difluorophenyl group, a 2,3,4-trifluorophenyl group, a 2,3,5-trifluorophenyl group, a 2,4,5-trifluorophenyl group, a 2,4,6-trifluorophenyl group, a 2,3,4,5-tetrafluorophenyl group, a 2,3,4,6-tetrafluorophenyl group, a 2,3,5,6-tetrafluorophenyl group, a 2,3,4,5,6-pentafluorophenyl group, etc.; a phenyl group substituted with a fluorine atom and an alkoxy group, such as a 2,4,5-trifluoro-3-methoxyphenyl group, a 2,4,5-trifluoro-3-ethoxyphenyl group, etc.

From the viewpoint of improving the low-temperature and high-temperature cycle property, the group has preferably at least two, more preferably at least three fluorine atoms; and the alkoxy group is preferably a methoxy group or an ethoxy group, more preferably a methoxy group.

Of the group represented by the above-mentioned general formula (II), more preferred is a 2,3,4-trifluorophenyl group, a 2,3,5-trifluorophenyl group, a 2,4,5-trifluorophenyl group, a 2,4,6-trifluorophenyl group, a 2,3,4,5-tetrafluorophenyl group, a 2,3,4,6-tetrafluorophenyl group, a 2,3,5,6-tetrafluorophenyl group, a 2,3,4,5,6-pentafluorophenyl group, or a 2,4,5-trifluoro-3-methoxyphenyl group.

Of the above-mentioned R$^1$, preferred are a hydrogen atom, a linear alkyl group having from 1 to 4 carbon atoms, a linear alkyl group having from 1 to 4 carbon atoms and substituted with a halogen atom, and, as the group represented by the general formula (II), a phenyl group substituted with only a fluorine atom, as improving the low-temperature and high-temperature cycle property; and more preferred are a hydrogen atom, a methyl group, an ethyl group and a trifluoromethyl group.

Of the above-mentioned R$^2$, preferred are a linear alkyl group having from 1 to 4 carbon atoms, a linear alkyl group having from 1 to 4 carbon atoms and substituted with a halogen atom, and, as the group represented by the general formula (II), a phenyl group substituted with only a fluorine atom, as improving the low-temperature and high-temperature cycle property; and more preferred are a methyl group, an ethyl group and a trifluoromethyl group.

Specific examples of the compound represented by the above-mentioned general formula (I) are mentioned below.

(i) Those where X is an alkylene group include 1,2-ethanediol formate methanesulfonate, 1,2-ethanediol formate ethanesulfonate, 1,2-ethanediol formate fluoromethanesulfonate, 1,2-ethanediol formate chloromethanesulfonate, 1,2-ethanediol acetate methanesulfonate, 1,2-ethanediol acetate ethanesulfonate, 1,2-ethanediol acetate fluoromethanesulfonate, 1,2-ethanediol acetate chloromethanesulfonate, 1,2-ethanediol acetate trifluoromethanesulfonate, 1,2-ethanediol methanesulfonate propionate, 1,2-ethanediol-2-fluorobenzoate methanesulfonate, 1,2-ethanediol-3-fluorobenzoate methanesulfonate, 1,2-ethanediol-4-fluorobenzoate methanesulfonate, 1,2-ethanediol-2,4-difluorobenzoate methanesulfonate, 1,2-ethanediol-2,6-difluorobenzoate methanesulfonate, 1,2-ethanediol-2,4,6-trifluorobenzoate methanesulfonate, 1,2-ethanediol-2,4,5-trifluoro-3-methoxybenzoate methanesulfonate, 1,2-ethanediol-2,4,5-trifluoro-3-methoxybenzoate 2,3,4,5,6-pentafluorobenzenesulfonate, 1,2-ethanediol-2,4,5-trifluoro-3-ethoxybenzoate methanesulfonate, 1,2-ethanediol-2,3,4,5,6-pentafluorobenzoate methanesulfonate, 1,2-propanediol formate methanesulfonate, 1,3-propanediol formate methanesulfonate, 1,3-butanediol formate methanesulfonate, 2-methyl-1,3-propanediol formate methanesulfonate, 1,4-pentanediol formate methanesulfonate, 1,4-butanediol formate methanesulfonate, 1,4-butanediol formate ethanesulfonate, 1,2-propanediol acetate methanesulfonate, 1,3-propanediol acetate methanesulfonate, 1,3-butanediol acetate methanesulfonate, 2-methyl-1,3-propanediol acetate methanesulfonate, 1,4-pentanediol acetate methanesulfonate, 1,4-butanediol acetate methanesulfonate, 1,4-butanediol acetate ethanesulfonate, 1,4-butanediol-2,4,5-trifluoro-3-methoxybenzoate methanesulfonate, 1,4-butanediol-2,4,5-trifluoro-3-methoxybenzoate 2,3,4,5,6-pentafluorobenzenesulfonate, 1,4-butanediol-2,3,4,5,6-pentafluorobenzoate methanesulfonate, 1,4-butanediol-2,3,4,5,6-pentafluorobenzoate 2,3,4,5,6-pentafluorobenzenesulfonate, 1,5-pentanediol acetate methanesulfonate, 1,6-hexanediol acetate methanesulfonate, etc.

Of the compounds where X is an alkylene group, preferred are 1,2-ethanediol acetate methanesulfonate, 1,2-ethanediol acetate ethanesulfonate, 1,2-ethanediol acetate trifluoromethanesulfonate, 1,2-ethanediol-2,4-difluorobenzoate methanesulfonate, 1,2-ethanediol-2,6-difluorobenzoate methanesulfonate, 1,2-ethanediol-2,4,6-trifluorobenzoate methanesulfonate, 1,2-ethanediol-2,4,5-trifluoro-3-methoxybenzoate methanesulfonate, 1,2-ethanediol-2,3,4,5,6-pentafluorobenzoate methanesulfonate, 1,2-propanediol-2,3,4,5,6-pentafluorobenzoate methanesulfonate, 1,3-propanediol-2,3,4,5,6-pentafluorobenzoate methanesulfonate, 1,3-propanediol acetate methanesulfonate, 1,4-butanediol formate methanesulfonate, 1,4-butanediol acetate methanesulfonate, 1,4-butanediol-2,3,4,5,6-pentafluorobenzoate methanesulfonate, 1,4-butanediol-2,3,4,5,6-pentafluorobenzoate 2,3,4,5,6-pentafluorobenzenesulfonate, and 1,6-hexanediol acetate methanesulfonate, from the viewpoint of improving the low-temperature and high-temperature cycle property. More preferred are 1,2-ethanediol acetate methanesulfonate, 1,2-ethanediol-2,4,5-trifluoro-3-methoxybenzoate methanesulfonate, 1,2-ethanediol-2,3,4,5,6-pentafluorobenzoate methanesulfonate, 1,2-propanediol-2,3,4,5,6-pentafluorobenzoate methanesulfonate, 1,3-propanediol-2,3,4,5,6-pentafluorobenzoate methanesulfonate, 1,3-propanediol acetate methanesulfonate, 1,4-butanediol acetate methanesulfonate, 1,6-hexanediol acetate methanesulfonate.

(ii) Those where X is an alkenylene group include 2-butene-1,4-diol formate methanesulfonate, 1,4-dimethyl-2-butene-1,4-diol formate methanesulfonate, 1,1,4,4-tetramethyl-2-butene-1,4-diol formate methanesulfonate, 2-pentene-1,5-diol formate methanesulfonate, 3-hexene-1,6-diol formate methanesulfonate, 2-butene-1,4-diol acetate methanesulfonate, 1,4-dimethyl-2-butene-1,4-diol acetate methanesulfonate, 1,1,4,4-tetramethyl-2-butene-1,4-diol acetate methanesulfonate, 2-pentene-1,5-diol acetate methanesulfonate, 3-hexene-1,6-diol acetate methanesulfonate, 2-butene-1,4-diol-2,4,5-trifluoro-3-methoxybenzoate methanesulfonate, 2-butene-1,4-diol-2,3,4,5,6-pentafluorobenzoate methanesulfonate, etc.

Of the compounds where x is an alkenylene group, preferred are 2-butene-1,4-diol formate methanesulfonate, 2-butene-1,4-diol acetate methanesulfonate, 2-butene-1,4-diol-2,4,5-trifluoro-3-methoxybenzoate methanesulfonate, and 2-butene-1,4-diol-2,3,4,5,6-pentafluorobenzoate methanesulfonate, from the viewpoint of improving the low-temperature and high-temperature cycle property. More preferred are 2-butene-1,4-diol formate methanesulfonate, 2-butene-1,4-diol acetate methanesulfonate, 2-butene-1,4-diol-2,4,5-trifluoro-3-methoxybenzoate methanesulfonate.

(iii) Those where X is an alkynylene group include 2-butyne-1,4-diol formate methanesulfonate, 1,4-dimethyl-2-butyne-1,4-diol formate methanesulfonate, 1,1,4,4-tetramethyl-2-butyne-1,4-diol formate methanesulfonate, 2-butyne-1,4-diol formate ethanesulfonate, 2-butyne-1,4-diol formate fluoromethanesulfonate, 2-butyne-1,4-diol formate chloromethanesulfonate, 2-butyne-1,4-diol formate trifluoromethanesulfonate, 2-butyne-1,4-diol formate 2,4,6-trifluorobenzenesulfonate, 2-butyne-1,4-diol formate 2,3,4,5,6-pentafluorobenzenesulfonate, 2-pentyne-1,5-diol formate methanesulfonate, 3-hexyne-1,6-diol formate methanesulfonate, 2-butyne-1,4-diol acetate methanesulfonate, 1,4-dimethyl-2-butyne-1,4-diol acetate methanesulfonate, 1,1,4,4-tetramethyl-2-butyne-1,4-diol acetate methanesulfonate, 2-butyne-1,4-diol acetate ethanesulfonate, 2-butyne-1,4-diol acetate fluoromethanesulfonate, 2-butyne-1,4-diol acetate chloromethanesulfonate, 2-butyne-1,4-diol acetate trifluoromethanesulfonate, 2-butyne-1,4-diol acetate 2,4,6-trifluorobenzenesulfonate, 2-butyne-1,4-diol acetate 2,3,4,5,6-pentafluorobenzenesulfonate, 2-butyne-1,4-diol methanesulfonate propionate, 2-pentyne-1,5-diol acetate methanesulfonate, 3-hexyne-1,6-diol acetate methanesulfonate, 2-butyne-1,4-diol-2-fluorobenzoate methanesulfonate, 2-butyne-1,4-diol-4-fluorobenzoate methanesulfonate, 2-butyne-1,4-diol-2,4-difluorobenzoate methanesulfonate, 2-butyne-1,4-diol-2,4,6-trifluorobenzoate methanesulfonate, 2-butyne-1,4-diol-2,4,5-trifluoro-3-methoxybenzoate methanesulfonate, 2-butyne-1,4-diol-2,4,5-trifluoro-3-methoxybenzoate 2,3,4,5,6-pentafluorobenzenesulfonate, 2-butyne-1,4-diol-2,4,5-trifluoro-3-ethoxybenzoate methanesulfonate, 2-butyne-1,4-diol-2,3,5,6-tetrafluorobenzoate methanesulfonate, 2-butyne-1,4-diol-2,3,4,5,6-pentafluorobenzoate methanesulfonate, 2-butyne-1,4-diol-2,3,4,5,6-pentafluorobenzoate 2,3,4,5,6-pentafluorobenzenesulfonate, etc.

Of the compounds where X is an alkynylene group, preferred are 2-butyne-1,4-diol formate methanesulfonate, 2-butyne-1,4-diol formate ethanesulfonate, 2-butyne-1,4-diol formate trifluoromethanesulfonate, 2-butyne-1,4-diol acetate methanesulfonate, 2-butyne-1,4-diol acetate ethanesulfonate, 2-butyne-1,4-diol acetate trifluoromethanesulfonate, 2-butyne-1,4-diol-2,4,5-trifluoro-3-methoxybenzoate methanesulfonate, 2-butyne-1,4-diol-2,3,4,5,6-pentafluorobenzoate methanesulfonate, and 2-butyne-1,4-diol-2,3,4,5,6-pentafluorobenzoate 2,3,4,5,6-pentafluorobenzenesulfonate, from the viewpoint of improving the low-temperature and high-temperature cycle property. More preferred are 2-butyne-1,4-diol formate methanesulfonate, 2-butyne-1,4-diol acetate methanesulfonate, 2-butyne-1,4-diol-2,4,5-trifluoro-3-methoxybenzoate methanesulfonate, 2-butyne-1,4-diol-2,3,4,5,6-pentafluorobenzoate methanesulfonate, 2-butyne-1,4-diol-2,3,4,5,6-pentafluorobenzoate 2,3,4,5,6-pentafluorobenzenesulfonate.

Of the compounds represented by the above-mentioned general formula (I), those that are especially preferred from the viewpoint of improving the low-temperature and high-temperature cycle property are 1,2-ethanediol acetate methanesulfonate, 1,2-ethanediol-2,4,5-trifluoro-3-methoxybenzoate methanesulfonate, 1,2-ethanediol-2,3,4,5,6-pentafluorobenzoate methanesulfonate, 1,3-propanediol acetate methanesulfonate, 1,4-butanediol acetate methanesulfonate, 2-butene-1,4-diol formate methanesulfonate, 2-butene-1,4-diol acetate methanesulfonate, 2-butyne-1,4-diol formate methanesulfonate, 2-butyne-1,4-diol acetate methanesulfonate, and 2-butyne-1,4-diol-2,4,5-trifluoro-3-methoxybenzoate methanesulfonate.

The content of at least one compound represented by the above-mentioned general formula (I) to be in the nonaqueous electrolytic solution of the present invention is from 0.01 to 10% by mass of the nonaqueous electrolytic solution. When the content is more than 10% by mass, then an excessive surface film may be formed on the electrode to thereby often lower the low-temperature cycle property of the battery; but when less than 0.01% by mass, then the formation of the surface film may be insufficient and the battery could not enjoy the effect of improving the high-temperature cycle property thereof. The content is preferably at least 0.1% by mass of the nonaqueous electrolytic solution, more preferably at least 0.5% by mass, even more preferably at least 1% by mass; and its upper limit is preferably at most 7% by mass, more preferably at most 5% by mass, even more preferably at most 3% by mass.

Even when the compound represented by the general formula (I) is used singly, the low-temperature and high-temperature cycle property can be improved; however, when the compound is combined with a nonaqueous solvent, an electrolyte salt and other additives mentioned below, then the electrolytic solution can exhibit a specific effect of synergistically improving the low-temperature and high-temperature cycle property of the battery. Though not always clear, the reason may be considered because a mixed surface film containing the compound represented by the general formula (I) and the constitutive elements of the nonaqueous solvent, the electrolyte salt or the other additives and having a high ionic conductivity may be formed.

Nonaqueous Solvent

The nonaqueous solvent for use in the nonaqueous electrolytic solution of the present invention includes cyclic carbonates, linear carbonates, linear esters, ethers, amides, phosphates, sulfones, lactones, nitriles, S=O bond-containing compounds, etc.

The cyclic carbonates include ethylene carbonate (EC), propylene carbonate (PC), butylene carbonate (BC), 4-fluoro-1,3-dioxolan-2-one (FEC), trans or cis-4,5-difluoro-1,3-dioxolan-2-one (the two are collectively referred to as "DFEC"), vinylene carbonate (VC), vinylethylene carbonate (VEC), etc. Of those, use of at lest one cyclic carbonate having a double bond or a fluorine atom is preferred as markedly improving the high-temperature cycle property; and a combination of a cyclic carbonate having a double bond and a cyclic carbonate having a fluorine atom is more preferred. As the double bond-containing cyclic carbonate, more preferred are VC and VEC; and as the fluorine-containing cyclic carbonate, more preferred are FEC and DFEC. Also preferred is use of PC as improving the low-temperature cycle property.

One type of those solvents may be used, but using two or more different types as combined is preferred as further improving the low-temperature and high-temperature cycle property. Even more preferably, three or more different types are combined. Preferred combinations of the cyclic carbonates include EC and VC; PC and VC; FEC and VC; FEC and EC; FEC and PC; FEC and DFEC; DFEC and EC; DFEC and PC; DFEC and VC; DFEC and VEC; EC and PC and VC; EC and FEC and VC; EC and VC and VEC; FEC and PC and VC; FEC and DFEC and EC; FEC and DFEC and PC; FEC and DFEC and VC; DFEC and PC and VC; DFEC and EC and VC; FEC and EC and PC and VC; DFEC and EC and PC and VC, etc. Of those combinations, more preferred combinations are EC and VC; FEC and PC; DFEC and PC; FEC and EC and PC; FEC and EC and VC; EC and VC and VEC; and FEC and EC and PC and VC.

Not specifically defined, the content of the cyclic carbonate is preferably within a range of from 10% by volume to 40% by volume relative to the total volume of the nonaqueous solvent. When the content is less than 10% by volume, then the conductivity of the nonaqueous electrolytic solution may lower, and the low-temperature and high-temperature cycle property may worsen; but when more than 40% by volume, then the viscosity of the nonaqueous electrolytic solution may increase and the low-temperature and high-temperature cycle property may worsen. Accordingly, the above range is preferred.

The linear carbonates include asymmetric linear carbonates such as methyl ethyl carbonate (MEC), methyl propyl carbonate, methyl isopropyl carbonate, methyl butyl carbonate, ethyl propyl carbonate, etc.; symmetric linear carbonates such as dimethyl carbonate (DMC), diethyl carbonate (DEC), dipropyl carbonate, dibutyl carbonate, etc. In particular, the asymmetric carbonates are preferred, as effectively improving the low-temperature cycle property. One type of those solvents may be used, but using two or more different types as combined is preferred as further improving the low-temperature and high-temperature cycle property.

Not specifically defined, the content of the linear carbonate is preferably within a range of from 60% by volume to 90% by volume relative to the total volume of the nonaqueous solvent. When the content is less than 60% by volume, then the viscosity of the nonaqueous electrolytic solution may increase and the low-temperature cycle property may worsen; but when more than 90% by volume, then the electric conductivity of the nonaqueous electrolytic solution may lower and the low-temperature and high-temperature cycle property may worsen. Accordingly, the above range is preferred.

The linear esters include methyl propionate, ethyl propionate, methyl acetate, ethyl acetate, methyl pivalate, butyl pivalate, hexyl pivalate, octyl pivalate, dimethyl oxalate, ethyl methyl oxalate, diethyl oxalate, etc. The ethers include tetrahydrofuran, 2-methyltetrahydrofuran, 1,3-dioxane, 1,4-dioxane, 1,2-dimethoxyethane, 1,2-diethoxyethane, 1,2-dibutoxyethane, etc.

The amides include dimethylformamide, etc.; the phosphates include trimethyl phosphate, tributyl phosphate, trioctyl phosphate, etc.; the sulfones include sulfolane, etc.; the lactones include γ-butyrolactone, γ-valerolactone, α-angelicalactone, etc.; the nitriles include mononitrile compounds such as acetonitrile, propionitrile, etc.; dinitrile compounds such as succinonitrile, glutaronitrile, adiponitrile, pimelonitrile, suberonitrile, etc.

The S=O bond-containing compounds include cyclic sulfite compounds such as ethylene sulfite, hexahydrobenzo[1,3,2]dioxathiol-2-oxide (this may be referred to also as 1,2-cyclohexanediol cyclic sulfite), 5-vinyl-hexahydro-1,3,2-benzodioxathiol-2-oxide, etc.; cyclic or linear sulfonate compounds such as 1,3-propanesultone (PS), 1,4-butanediol dimethanesulfonate, 1,3-butanediol dimethanesulfonate, 1,2-propanediol dimethanesulfonate, etc.; sulfone compounds such as divinyl sulfone, 1,2-bis(vinylsulfonyl)ethane, bis(2-vinylsulfonylethyl) ether, etc.

Of the above-mentioned nonaqueous solvents, preferred is a combination of the nitrile or the S=O bond-containing compound and the compound represented by the general formula (I) as improving the high-temperature cycle property; and more preferred is a combination of a dinitrile compound or a cyclic sulfite compound and the compound represented by the general formula (I).

When the amount of the additive compound to be combined with the compound represented by the general formula (I) in the nonaqueous electrolytic solution is more than 5% by mass of the solution, then the low-temperature cycle property may worsen or the solution could not exhibit the effect of improving the high-temperature cycle property; but when less than 0.1% by mass, then the effect of improving the low-temperature and high-temperature cycle property could not be sufficiently attained. Accordingly, the content is preferably at least 0.1% by mass of the nonaqueous electrolytic solution, more preferably at least 0.3% by mass. The upper limit of the content is preferably at most 5% by mass, more preferably at most 3% by mass.

In general, the nonaqueous solvents are used as a mixture thereof for attaining the suitable physical properties. Regarding their combinations, for example, there are mentioned a combination of a cyclic carbonate and a linear carbonate, a combination of a cyclic carbonate, a linear carbonate and a lactone, a combination of a cyclic carbonate, a linear carbonate and an ether, a combination of a cyclic carbonate, a linear carbonate and a linear ester, a combination of a cyclic carbonate, a linear carbonate and a nitrile, a combination of a cyclic carbonate, a linear carbonate and an S=O bond-containing compound, etc.

Of those, preferred is using a nonaqueous solvent of a combination of at least a cyclic carbonate and a linear carbonate, as effectively improving the low-temperature and high-temperature cycle property. The ratio of the cyclic carbonate to the linear carbonate is not specifically defined. Preferably, the ratio (by volume) of cyclic carbonate/linear carbonate is from 10/90 to 40/60, more preferably from 15/85 to 35/65, even more preferably from 20/80 to 30/70.

[Electrolyte Salt]

The electrolyte salt for use in the present invention includes lithium salts such as $LiPF_6$, $LiBF_4$, $LiClO_4$, $LiPO_2F_2$, etc.; linear fluoroalkyl group-having lithium salts such as $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$ etc.; cyclic fluoroalkylene chain-having lithium salts such as $(CF_2)_2(SO_2)_2NLi$, $(CF_2)_3(SO_2)_2NLi$, etc.; and lithium salts with an anion of an oxalate complex such as lithium bis[oxalate-O,O']borate, lithium difluoro[oxalate-O,O']borate, etc. Of those, especially preferred electrolyte salts are $LiPF_6$, $LiBF_4$, $LiN(SO_2CF_3)_2$, and $LiN(SO_2C_2F_5)_2$. One or more of these electrolyte salts may be used herein either singly or as combined.

A preferred combination of these electrolyte salts is a combination containing $LiPF_6$ as combined with at least one selected from $LiBF_4$, $LiN(SO_2CF_3)_2$ and $LiN(SO_2C_2F_5)_2$. Preferred are a combination of $LiPF_6$ and $LiBF_4$; a combination of $LiPF_6$ and $LiN(SO_2CF_3)_2$; a combination of $LiPF_6$ and $LiN(SO_2C_2F_5)_2$, etc.

When the ratio (by mol) of $LiPF_6/[LiBF_4$ or $LiN(SO_2CF_3)_2$ or $LiN(SO_2C_2F_5)_2]$ is smaller than 70/30 in point of the proportion of $LiPF_6$, or when the ratio is larger than 99/1 in point of the proportion of $LiPF_6$, then the low-temperature and high-temperature cycle property may worsen. Accordingly, the ratio (by mol) of $LiPF_6/[LiBF_4$ or $LiN(SO_2CF_3)_2$ or $LiN(SO_2C_2F_5)_2]$ is preferably within a range of from 70/30 to 99/1, more preferably from 80/20 to 98/2. The combination falling within the above range is more effective for improving the battery characteristics of low-temperature and high-temperature cycle property.

The concentration of all these electrolyte salts as dissolved in the solution is generally preferably at least 0.3 M relative to the above-mentioned nonaqueous solvent, more preferably at least 0.5 M, even more preferably at least 0.7 M. The upper limit of the concentration is preferably at most 2.5 M, more preferably at most 2.0 M, even more preferably at most 1.5 M.

As the electrolyte for electric double layer capacitors (condensers), usable are known quaternary ammonium salts such as tetraethylammonium tetrafluoroborate, triethylmethylammonium tetrafluoroborate, tetraethylammonium hexafluorophosphate, etc.

[Other Additives]

An aromatic compound may be added to the nonaqueous electrolytic solution of the present invention, thereby securing the safety of the battery in overcharging. Preferred examples of the aromatic compound include cyclohexylbenzene, fluorocyclohexylbenzene compound (1-fluoro-2-cyclohexylbenzene, 1-fluoro-3-cyclohexylbenzene, 1-fluoro-4-cyclohexylbenzene), tert-butylbenzene, tert-amylbenzene, 1-fluoro-4-tert-butylbenzene, 1,3-di-tert-butylbenzene, biphenyl, terphenyl (o-, m-, p-form), diphenyl ether, fluorobenzene, difluorobenzene (o-, m-, p-form), 2,4-difluoroanisole, partially hydrogenated terphenyl (1,2-dicyclohexylbenzene, 2-phenylbicyclohexyl, 1,2-diphenylcyclohexane, o-cyclohexylbiphenyl), etc. One or more of these compounds may be used herein either singly or as combined.

[Production of Nonaqueous Electrolytic Solution]

The nonaqueous electrolytic solution of the present invention can be produced, for example, by mixing the above-mentioned nonaqueous solvents followed by dissolving therein the above-mentioned electrolyte salt and at least one compound represented by the above-mentioned general formula (I) in an amount of from 0.01 to 10% by mass of the resulting nonaqueous electrolytic solution.

In this case, the nonaqueous solvent to be used, and the compound to be added to the nonaqueous electrolytic solution are preferably previously purified within a range not significantly detracting from the producibility, in which, therefore, the impurity content is preferably as low as possible.

The nonaqueous electrolytic solution of the present invention is favorably used for the electrolytic solution for lithium primary batteries and lithium secondary batteries. Further, the nonaqueous electrolytic solution of the present invention is also usable as an electrolytic solution for electric double layer capacitors or as an electrolytic solution for hybrid capacitors. Of those, the nonaqueous electrolytic solution of the present invention is most favorable for lithium secondary batteries.

[Lithium Battery]

The lithium battery of the present invention collectively includes a lithium primary battery and a lithium secondary battery, comprising a positive electrode, a negative electrode and the above-mentioned nonaqueous electrolytic solution of an electrolyte salt dissolved in a nonaqueous solvent, and is characterized in that the nonaqueous electrolytic solution contains at least one compound represented by the above-mentioned general formula (I) in an amount of from 0.01 to 10% by mass of the solution.

In the lithium battery of the present invention, the other constitutive components such as the positive electrode and the negative electrode except for the nonaqueous electrolytic solution can be used with no limitation.

For example, as the positive electrode active material for lithium secondary battery, usable are complex metal oxides of lithium containing any of cobalt, manganese or nickel. One or more such positive electrode active materials may be used either singly or as combined.

The complex metal oxides include, for example, $LiCoO_2$, $LiMn_2O_4$, $LiNiO_2$, $LiCO_{1-x}Ni_xO_2$ $(0.01<x<1)$, $LiCO_{1/3}Ni_{1/3}Mn_{1/3}O_2/LiNi_{1/2}Mn_{3/2}O_4$, $LiMn_2O_2$, etc. Combinations of $LiCoO_2$ and $LiMn_2O_4$; $LiCoO_2$ and $LiNiO_2$; $LiMn_2O_4$ and $LiNiO_2$ are acceptable herein.

For enhancing the safety in overcharging or enhancing the cycle property, the lithium complex oxide may be partly substituted with any other element for enabling the use of the battery at a charging potential of 4.3 V or more. For example, a part of cobalt, manganese and nickel may be substituted with at least one element of Sn, Mg, Fe, Ti, Al, Zr, Cr, V, Ga, Zn, Cu, Bi, Mo, La, etc.; or O may be partly substituted with S or F; or the oxide containing such other element may be coated.

Of those, preferred are lithium complex metal oxides such as $LiCoO_2$, $LiMn_2O_4$ and $LiNiO_2$, with which the positive electrode charging potential in a fully-charged state may be 4.3 V or more, based on Li. More preferred are lithium complex oxides usable at 4.4 V or more, such as $LiCO_{1-x}M_xO_2$ (where M is at least one element of Sn, Mg, Fe, Ti, Al, Zr, Cr, V, Ga, Zn and Cu; $0.001 \leq x \leq 0.05$), $LiCO_{1/3}Ni_{1/3}Mn_{1/3}O_2$, and $LiNi_{1/2}Mn_{3/2}O_4$.

Further, lithium-containing olivine-type phosphates are also usable as the positive electrode active material. Their concrete examples include $LiFePO_4$, $LiCoPO_4$, $LiNiPO_4$, $LiMnPO_4$, etc.

The lithium-containing olivine-type phosphates may be partly substituted with any other element. For example, a part of iron, cobalt, nickel and manganese therein may be substituted with at least one element selected from Co, Mn, Ni, Mg, Al, B, Ti, V, Nb, Cu, Zn, Mo, Ca, Sr, W and Zr; or the phosphates may be coated with a compound containing any of these other elements or with a carbon material. Of those, preferred are $LiFePO_4$ and $LiMnPO_4$. The lithium-containing olivine-type phosphate may be combined with, for example, the above-mentioned positive electrode active materials.

Not specifically defined, the electroconductive agent of the positive electrode may be any electron-transmitting material not undergoing chemical change. For example, it includes graphites such as natural graphite (flaky graphite, etc.), artificial graphite, etc.; carbon blacks such as acetylene black, Ketjen black, channel black, furnace black, lamp black, thermal black, etc. Graphites and carbon blacks combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent such as acetylene black, carbon black or the like, and with a binder such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling-point solvent such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 g/cm³, and for further increasing the capacity of the battery, the density is preferably at least 2.5 g/cm³, more preferably at least 3.5 g/cm³. When more than 4.0 g/cm³, however, the formation may be substantially difficult, and therefore, the upper limit is preferably at most 4.0 g/cm³.

For the positive electrode for lithium primary battery, there are mentioned oxides or chalcogen compounds of one or more metal elements such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_5O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds such as $SO_2$, $SOCl_2$, etc.; carbon fluorides (fluorographite) represented by a general formula $(CF_x)_n$, etc. Of those, preferred are $MnO_2$, $V_2O_5$, fluorographite, etc.

As the negative electrode active material for lithium secondary battery, usable are one or more of lithium metal, lithium alloys, carbon materials [graphites such as artificial graphite, natural graphite, etc.;], tin, tin compounds, silicon, silicon compounds and the like capable of absorbing and releasing lithium, either singly or as combined.

Of those, preferred is use of high-crystalline carbon materials in view of the ability thereof to absorb and release lithium ions, and preferred is use of a carbon material having a graphite-type crystal structure where the lattice (002) spacing ($d_{002}$) is at most 0.340 nm (nanometers), especially from 0.335 to 0.337 nm. More preferably, the high-crystalline carbon material is coated with a low-crystalline carbon material. When such a high-crystalline carbon material is used, then it may react with a nonaqueous electrolytic solution in charging thereby worsening the low-temperature and high-temperature cycle property; however, in the lithium secondary battery of the present invention, the reaction with the nonaqueous electrolytic solution can be retarded.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of simple substances, alloys, oxides, nitrides, sulfides, borides, alloys with lithium or the like; but preferred are any of simple substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the capacity of the battery.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

In case where graphite is used as the negative electrode active material, the density of the part except the collector of the negative electrode may be generally at least 1.4 g/cm$^3$, and for further increasing the capacity of the battery, the density is preferably at least 1.6 g/cm$^3$, more preferably at least 1.7 g/cm$^3$. When more than 2.0 g/cm$^3$, however, the formation may be substantially difficult, and therefore, the upper limit is preferably at most 2.0 g/cm$^3$.

As the negative electrode active material for lithium primary battery, usable is a lithium metal or a lithium alloy.

As the separator for battery, usable is a single-layer or laminate porous film of polyolefin such as polypropylene, polyethylene or the like, as well as a woven fabric, a non-woven fabric, etc.

The structure of the lithium secondary battery is not specifically defined. The battery may be a coin-shaped battery, a cylindrical battery, a square-shaped battery, or a laminate-type battery, each having a single-layered or multi-layered separator.

The lithium secondary battery of the present invention exhibits excellent long-term cycle property even when the final charging voltage is 4.2 V or higher and particularly 4.3 V or higher. Furthermore, the cycle property is good even when the final charging voltage is 4.4 V. The final discharging voltage can be 2.5 V or more and further 2.8 V or more. The current value is not specifically defined. In general, the current mode is a constant current discharging mode within a range of from 0.1 to 3 C. The lithium secondary battery of the present invention may be charged and discharged at the range from −40° C. to 100° C. and preferably at the range from 0° C. to 80° C.

In the present invention, as a countermeasure against the increase in the internal pressure of the lithium secondary battery, there may be employed a method of providing a safety valve in the battery cap or a method of forming a cutout in the battery component such as the battery can, the gasket or the like. In addition, as a safety countermeasure against overcharging, a current breaker capable of detecting the internal pressure of the battery to cut off the current may be provided in the battery cap.

[Formyloxy Group-Containing Compound]

The formyloxy group-containing compound of the present invention is represented by the following general formula (III):

[Formula 5]

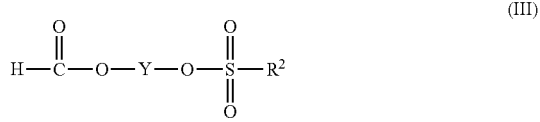

In the general formula (III), Y represents a linear or branched alkenylene group having from 4 to 8 carbon atoms, or a linear or branched alkynylene group having from 4 to 8 carbon atoms. R$^2$ has the same meaning as above, representing a linear or branched alkyl group having from 1 to 6 carbon atoms, a cycloalkyl group having from 3 to 8 carbon atoms, or a group of the above-mentioned general formula (II). However, at least one hydrogen atom of the alkyl group may be substituted with a halogen atom.

Specific examples and preferred examples of the alkenylene group and the alkynylene group for Y, and specific examples and preferred examples of the alkyl group, the cycloalkyl group and the group represented by the general formula (II) for R$^2$ are the same as those mentioned hereinabove for the general formula (I).

The formyloxy group-containing compound represented by the general formula (III) may be produced according to the methods (i) to (viii) mentioned below, to which, however, the present invention is not limited.

(i) A method of condensing a hydroxysulfonate with formic acid in the presence or absence of a solvent, in the presence or absence of an acid catalyst, and optionally in the presence of a dehydrating agent.

(ii) A method of transesterifying a hydroxysulfonate with a formate in the presence or absence of a solvent, and in the presence of an acid catalyst.

(iii) A method of esterifying a hydroxysulfonate with an acid anhydride in the presence or absence of a solvent.

(iv) A method of esterifying a hydroxyformate with a sulfonic acid halide or a sulfonic acid anhydride in the presence or absence of a solvent.

(v) A method of transesterifying a dimethanesulfonate with formic acid or a formate anion in the presence or absence of a solvent and in the presence or absence of a catalyst.

(vi) A method of transesterifying a diformate with methanesulfonic acid or a methanesulfonate anion in the presence or absence of an acid catalyst and in the presence or absence of a catalyst.

(vii) A method of transesterifying a trimethanesulfonate formic acid or a formate anion in the presence or absence of a solvent, and in the presence or absence of a catalyst.

(viii) A method of transesterifying a triformate with methanesulfonic acid or a methanesulfonate anion in the presence or absence of an acid catalyst and in the presence or absence of a catalyst.

EXAMPLES

Production Examples for the novel formyloxy group-containing compound of the present invention, and Examples of a lithium ion secondary battery comprising the nonaqueous electrolytic solution of the present invention are shown below; however, the present invention should not be restricted by these Production Examples and Examples.

Production Example 1

41.5 g (0.409 mol) of triethylamine was added to 300 ml of dimethyl carbonate solution of 44.0 g (0.386 mol) of 4-formyloxy-2-butyn-1-ol, and cooled to 0° C. 46.9 g (0.409 mol) of methanesulfonyl chloride was dropwise added to the solution while the inner temperature was controlled to be not higher than 15° C. After the addition, this was stirred at 25° C. for 1.5 hours, the reaction mixture was poured into an aqueous saturated sodium bicarbonate solution, the aqueous layer was separated, and the organic layer was concentrated to give 72.6 g (yield 98%) 4-formyloxy-2-butyn-1-yl methanesulfonate. For use in the battery test, this was purified through silica gel column chromatography.

Thus obtained, 4-formyloxy-2-butyn-1-yl methanesulfonate (this is the same as 2-butyne-1,4-diol formate methanesulfonate) was analyzed through $^1$H-NMR (measuring instrument, JEOL's "AL-300"), mass spectrometry (measuring instrument, Hitachi's "M80B") and IR absorptiometry (measuring instrument, Varian's "Varian 3100") to identify the structure thereof.

(1) $^1$H-NMR (300 MHz, CDCl$_3$): δ=8.07 (t, J=0.97 Hz, 1H), 4.90 (t, J=1.95 Hz, 2H), 4.83 (td, J=1.95, 0.97 Hz, 2H), 3.13 (s, 3H).
(2) Mass Spectrometry: MS (CI) [M+1]=193.
(3) IR (neat): 3030, 2943, 1728, 1439, 1355, 1174, 976, 948, 807, 715 cm$^{-1}$ Production Example 2

20.0 g (0.217 mol) of glycerin, 21.0 g (0.456 mol) of formic acid and 0.21 g (0.002 mol) of methanesulfonic acid were dissolved in 20 ml of diisopropyl ether and reacted for azeotropic dehydration at 80° C. for 4 hours, in which the disappearance of glycerin was confirmed. The reaction liquid was concentrated, and purified through silica gel column chromatography to give 20.0 g of a mixture of 1,3-bis(formyloxy)-2-propanol and 2,3-bis(formyloxy)-1-propanol (yield, 64%). 20.0 g (0.140 mol) of the mixture and 14.8 g (0.147 mol) of triethylamine were dissolved in 200 ml of ethyl acetate, cooled to 0° C., then 16.4 g (0.147 mol) of methanesulfonyl chloride was dropwise added thereto, taking 15 minutes, and this was stirred at 25° C. for 1 hour. The precipitated triethylamine hydrochloride was removed through filtration, the filtrate was concentrated, and the resulting mixture was purified through silica gel column chromatography to give 7.0 g (yield 14%) of 1,3-bis(formyloxy)-2-propyl methanesulfonate and 20.1 g (yield, 41%) of 2,3-bis(formyloxy)-1-propyl methanesulfonate.

Structure identification of
1,3-bis(formyloxy)-2-propyl methanesulfonate
[namely,
glycerol-1,3-diformate-2-methanesulfonate]

(1) $^1$H-NMR (300 MHz, CDCl$_3$): δ=8.10 (d, J=0.49 Hz, 2H), 5.49-5.42 (m, 1H), 4.47-4.31 (m, 4H), 3.07 (s, 3H).
(2) Mass Spectrometry: MS (CI) [M++1]=227.

Structure identification of
2,3-bis(formyloxy)-1-propyl methanesulfonate
[namely,
glycerol-2,3-diformate-1-methanesulfonate]

(1) $^1$H-NMR (300 MHz, CDCl$_3$): δ=8.10 (d, J=0.49 Hz, 2H), 5.12-5.05 (m, 1H), 4.52-4.34 (m, 4H), 3.12 (s, 3H).
(2) Mass Spectrometry: MS (CI) [M++1]=227.

Examples 1 to 19, and Comparative Examples 1 to 3

(1) Production of Lithium Ion Secondary Battery

93% by mass of LiCoO$_2$ (positive electrode active material) and 3% by mass of acetylene black (electroconductive agent) were mixed, and added to and mixed with a solution previously prepared by dissolving 4% by mass of polyvinylidene fluoride (binder) in 1-methyl-2-pyrrolidone, thereby preparing a positive electrode mixture paste. The positive electrode mixture paste was applied onto both surfaces of an aluminium foil (collector), dried, processed under pressure and cut into a predetermined size, thereby producing a long rectangular, positive electrode sheet. The density of a part of the positive electrode except the collector was 3.6 g/cm$^3$.

On the other hand, 95% by mass of artificial graphite (d$_{002}$=0.335 nm, negative electrode active material) coated with low-crystalline carbon was added to and mixed with a solution previously prepared by dissolving 5% by mass of polyvinylidene fluoride (binder) in 1-methyl-2-pyrrolidone, thereby preparing a negative electrode mixture paste. The negative electrode mixture paste was applied onto both surfaces of a copper foil (collector), dried, processed under pressure and cut into a predetermined size, thereby producing a long rectangular, negative electrode sheet. The density of a part of the negative electrode except the collector was 1.7 g/cm$^3$. The positive electrode sheet, a porous polyethylene film separator, the negative electrode sheet and a separator were laminated in that order, and the resulting laminate was coiled up. The coil was housed into a nickel-plated, iron-made cylindrical battery can serving also as a negative electrode terminal.

Next, a nonaqueous electrolytic solution that had been prepared by adding a predetermined amount of the compound described in Table 1 was injected into the battery can, which was calked with a battery cap having a positive electrode terminal, via a gasket therebetween, thereby fabricating a 18650-type cylindrical battery. The positive electrode terminal was connected to the positive electrode sheet via an aluminium lead tab therebetween; and the negative electrode can was previously connected to the negative electrode sheet inside the battery, via a nickel lead tab therebetween.

(2) Evaluation of High-Temperature and
Low-Temperature Cycle Property

In a thermostat chamber kept at 25° C., the battery fabricated in the above (1) was charged up to 4.2 V (charging final voltage) with a constant current of 1 C, then charged for 2.5 hours at the constant voltage of 4.2 V, and thereafter this was discharged under a constant current of 1 C to a discharge voltage of 3.0 V (discharging final voltage), and the discharge capacity in one cycle was measured.

Next, in a thermostat chamber kept at 60° C., the battery was charged up to 4.2 V (charging final voltage) with a constant current of 1 C, then charged for 2.5 hours at the constant voltage of 4.2 V, and thereafter this was discharged under a constant current of 1 C to a discharge voltage of 3.0 V (discharging final voltage). This was repeated to a total of 50 cycles.

Next, in a thermostat chamber kept at 0° C., the battery was charged up to 4.2 V with a constant current of 1 C, then charged for 2.5 hours at the constant voltage of 4.2 V, and thereafter this was discharged under a constant current of 1 C to a discharge voltage of 3.0 V. This was repeated to a total of 50 cycles.

Next, in a thermostat chamber kept at 25° C., the battery was charged up to 4.2 V (charging final voltage) with a constant current of 1 C, then charged for 2.5 hours at the constant voltage of 4.2 V, and thereafter this was discharged under a constant current of 1 C to a discharge voltage of 3.0 V (discharging final voltage). After the high-temperature and low-temperature cycles, the recovered discharge capacity was measured. According to the following formula, the discharge capacity retention rate (%) of the battery after the high-temperature and low-temperature cycles was determined. The results are shown in Table 1-1 and Table 1-2.

Discharge Capacity Retention Rate (%) after high-temperature and low-temperature cycles=[recovered discharge capacity after high-temperature and low-temperature cycles/discharge capacity in first cycle]×100

TABLE 1-1

| | Composition of Electrolyte Salt Composition of Nonaqueous Electrolytic Solution (solvent ratio by volume) | Added Compound (content (%) in nonaqueous electrolytic solution) | Discharge Capacity Retention Rate (%) after high-temperature and low-temperature cycles |
|---|---|---|---|
| Example 1 | 1M LiPF6 EC/VC/MEC (28/2/70) | 1,2-ethanediol-2,3,4,5,6-pentafluorobenzoate methanesulfonate (0.1) | 73 |
| Example 2 | 1M LiPF6 EC/VC/MEC (28/2/70) | 1,2-ethanediol-2,3,4,5,6-pentafluorobenzoate methanesulfonate (1) | 79 |
| Example 3 | 1M LiPF6 EC/VC/MEC (28/2/70) | 1,2-ethanediol-2,3,4,5,6-pentafluorobenzoate methanesulfonate (4) | 77 |
| Example 4 | 1M LiPF6 EC/VC/MEC (28/2/70) | 1,2-ethanediol-2,3,4,5,6-pentafluorobenzoate methanesulfonate (7) | 75 |
| Example 5 | 1M LiPF6 EC/VC/MEC (28/2/70) | 1,2-ethanediol acetate methanesulfonate (1) | 77 |
| Example 6 | 1M LiPF6 EC/VC/MEC (28/2/70) | 1,2-ethanediol-2,4,5-trifluoro-3-methoxybenzoate methanesulfonate (1) | 75 |
| Example 7 | 1M LiPF6 EC/VC/MEC (28/2/70) | 2-butyne-1,4-diol-2,4,5-trifluoro-3-methoxybenzoate methanesulfonate (1) | 73 |
| Example 8 | 1M LiPF6 EC/VC/MEC (28/2/70) | 2-buten-1,4-diol acetate methanesulfonate (1) | 69 |
| Example 9 | 1M LiPF6 EC/VC/MEC (28/2/70) | 2-butyne-1,4-diol acetate methanesulfonate (1) | 75 |
| Example 10 | 1M LiPF6 EC/VC/MEC (28/2/70) | 2-butyne-1,4-diol formate methanesulfonate (1) | 80 |
| Example 11 | 1M LiPF6 EC/VC/MEC (28/2/70) | glycerol-1,3-diformate-2-methanesulfonate (1) | 72 |
| Example 12 | 1M LiPF6 EC/VC/MEC (28/2/70) | glycerol-2,3-diformate-1-methanesulfonate (1) | 71 |
| Comparative Example 1 | 1M LiPF6 EC/VC/MEC(28/2/70) | none | 65 |
| Comparative Example 2 | 1M LiPF6 EC/VC/MEC(28/2/70) | ethylene glycol diacetate (1) | 64 |
| Comparative Example 3 | 1M LiPF6 EC/VC/MEC (28/2/70) | 2-butyne-1,4-diol diacetate (0.5) 2-butyne-1,4-diol dimethanesulfonate (0.5) | 66 |

TABLE 1-2

| | Composition of Electrolyte Salt Composition of Nonaqueous Electrolytic Solution (solvent ratio by volume) | Added Compound (content (%) in nonaqueous electrolytic solution) | Discharge Capacity Retention Rate (%) after high-temperature and low-temperature cycles |
|---|---|---|---|
| Example 13 | 0.95M LiPF6 + 0.05M LiN(SO2CF3)2 FEC/PC/MEC/DMC (20/5/50/25) | 2-butyne-1,4-diol acetate methanesulfonate (1) | 82 |
| Example 14 | 0.95M LiPF6 + 0.05M LiBF4 EC/PC/DFEC/MEC/DMC (15/5/5/50/25) | 2-butyne-1,4-diol acetate methanesulfonate (1) | 79 |
| Example 15 | 0.95M LiPF6 + 0.05M LiN(SO2CF3)2 EC/VC/VEC/MEC/DMC (27/2/1/50/20) | 2-butyne-1,4-diol acetate methanesulfonate (1) | 78 |
| Example 16 | 0.95M LiPF6 + 0.05M LiN(SO2CF3)2 EC/PC/FEC/VC/MEC (23/5/1/1/70) | 1,4-butanediol formate methanesulfonate (1) | 75 |

TABLE 1-2-continued

| | Composition of Electrolyte Salt Composition of Nonaqueous Electrolytic Solution (solvent ratio by volume) | Added Compound (content (%) in nonaqueous electrolytic solution) | Discharge Capacity Retention Rate (%) after high-temperature and low-temperature cycles |
|---|---|---|---|
| Example 17 | 0.95M LiPF6 + 0.05M LiN(SO2CF3)2 EC/PC/FEC/VC/MEC (23/5/1/1/70) | 2-butyne-1,4-diol formate methanesulfonate (1) | 83 |
| Example 18 | 0.95M LiPF6 + 0.05M LiN(SO2CF3)2 FEC/DFEC/VC/MEC (28/1/1/70) | 2-butyne-1,4-diol formate methanesulfonate (1) + adiponitrile (1) | 84 |
| Example 19 | 0.95M LiPF6 + 0.05M LiN(SO2CF3)2 FEC/DFEC/VC/MEC (28/1/1/70) | 2-butyne-1,4-diol formate methanesulfonate (1) + 1,2-cyclohexanediol cyclic sulfite (1) | 84 |

Example 20, Comparative Example 4

A positive electrode sheet was produced, using LiFePO$_4$ (positive electrode active material) in place of the positive electrode active material used in Example 1. 90% by mass of LiFePO$_4$ and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste.

Using the nonaqueous electrolytic solution described in Table 2, a cylindrical battery was fabricated in the same manner as in Example 1, for which, however, the above positive electrode mixture paste was applied onto an aluminium foil (collector), dried, processed under pressure and cut into a predetermined size, thereby preparing a long rectangular positive electrode sheet, the final charging voltage was 3.6 V, and the final discharging voltage was 2.0 V; and the battery was evaluated. The results are shown in Table 2.

TABLE 2

| | Composition of Electrolyte Salt Composition of Nonaqueous Electrolytic Solution (solvent ratio by volume) | Added Compound (content (%) in electrolytic solution) | Discharge Capacity Retention Rate (%) after high-temperature and low-temperature cycles |
|---|---|---|---|
| Example 20 | 1M LiPF6 EC/VC/MEC (28/2/70) | 1,2-ethanediol-2,3,4,5,6-pentafluorobenzoate methanesulfonate (1) | 76 |
| Comparative Example 4 | 1M LiPF6 EC/VC/MEC (28/2/70) | none | 62 |

Example 21, Comparative Example 5

A negative electrode sheet was produced, using Si (negative electrode active material) in place of the negative electrode active material used in Example 1. 80% by mass of Si and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste.

Using the nonaqueous electrolytic solution described in Table 3, a cylindrical battery was fabricated in the same manner as in Example 1, for which, however, the above negative electrode mixture paste was applied onto a copper foil (collector), dried, processed under pressure and cut into a predetermined size, thereby preparing a long rectangular negative electrode sheet; and the battery was evaluated. The results are shown in Table 3.

TABLE 3

| | Composition of Electrolyte Salt Composition of Nonaqueous Electrolytic Solution (solvent ratio by volume) | Added Compound (content (%) in electrolytic solution) | Discharge Capacity Retention Rate (%) after high-temperature and low-temperature cycles |
|---|---|---|---|
| Example 21 | 1M LiPF6 EC/VC/MEC (28/2/70) | 1,2-ethanediol-2,3,4,5,6-pentafluorobenzoate methanesulfonate (1) | 69 |
| Comparative Example 5 | 1M LiPF6 EC/VC/MEC (28/2/70) | none | 57 |

The lithium secondary batteries of Examples 1 to 19 are all greatly improved in point of the low-temperature and high-temperature cycle property, as compared with the lithium secondary batteries of Comparative Example 1 (to which the compound of the present invention is not added), Comparative Example 2 (in which a compound having two and the same substituents bonded via a hydrocarbon group is used) and Comparative Example 3 (in which two and different types of compounds each having two and the same substituents bonded via a hydrocarbon group are mixed and used). From the results, it is known that the compound having a structure where two and different substituents are bonded via a hydrocarbon group brings about an unexpected specific effect.

From comparison between Example 20 and Comparative Example 4 and comparison between Example 21 and Comparative Example 5, the same effect is also seen in the case where a lithium-containing olivine-type iron phosphate is used for the positive electrode and in the case where Si is used for the negative electrode. Accordingly, it is known that the effect of the present invention does not depend on a specific positive electrode or negative electrode.

INDUSTRIAL APPLICABILITY

The lithium battery comprising the nonaqueous electrolytic solution of the present invention is useful as a battery having an excellent low-temperature and high-temperature cycle property.

The formyloxy group-containing compound represented by the general formula (III) is useful as an additive to lithium batteries, and is also usable as intermediate materials for medicines, agricultural chemicals, electronic materials, polymer materials, etc.

The invention claimed is:

1. A nonaqueous electrolytic solution for a lithium battery, comprising:
   a nonaqueous solvent; and
   an electrolyte dissolved in the nonaqueous solvent;
   wherein
   the nonaqueous solvent comprises from 0.01 to 10% by mass of at least one compound selected from the group consisting of a compound of formula (I), 1,2-ethanediol acetate methanesulfonate, 1,3-propanediol acetate methanesulfonate, 1,4-butanediol acetate methanesulfonate, and 2-butene-1,4-diol acetate methanesulfonate:

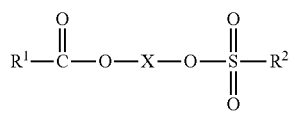
(I)

wherein
X is an alkylene group having from 1 to 6 carbon atoms, an alkenylene group having from 4 to 8 carbon atoms, or an alkynylene group having from 4 to 8 carbon atoms;
$R^1$ is a hydrogen atom, or a group of formula (II);
$R^2$ is an alkyl group having from 1 to 6 carbon atoms, a cycloalkyl group having from 3 to 8 carbon atoms, or a group of formula (II); with the proviso that at least one hydrogen atom of the alkyl group is optionally substituted with a halogen atom;

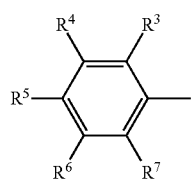
(II)

wherein $R^3$ to $R^7$ are each independently a hydrogen atom, a fluorine atom, a methoxy group, or an ethoxy group.

2. The nonaqueous electrolytic solution for lithium battery according to claim 1, wherein the nonaqueous solvent comprises a cyclic carbonate and a linear carbonate.

3. The nonaqueous electrolytic solution for lithium battery according to claim 2, wherein the cyclic carbonate is at least one selected from the group consisting of ethylene carbonate, propylene carbonate, butylene carbonate and a cyclic carbonate having a double bond or a fluorine atom.

4. The nonaqueous electrolytic solution for lithium battery according to claim 3, wherein the cyclic carbonate having a double bond or a fluorine atom is vinylene carbonate, vinylethylene carbonate, 4-fluoro-1,3-dioxolane-2-one, or 4,5-difluoro-1,3-dioxolane-2-one.

5. The nonaqueous electrolytic solution for lithium battery according to claim 2, wherein the linear carbonate is at least one selected from the group consisting of methyl ethyl carbonate, methyl propyl carbonate, methyl isopropyl carbonate, methyl butyl carbonate, and ethyl propyl carbonate.

6. The nonaqueous electrolytic solution for lithium battery according to claim 1, wherein the electrolyte comprises $LiPF_6$, and at least one selected from the group consisting of $LiBF_4$, $LiN(SO_2CF_3)_2$ and $LiN(SO_2C_2F_5)_2$.

7. The nonaqueous electrolytic solution for lithium battery according to claim 6, wherein a mole ratio of $LiPF_6$ to the at least one selected from $LiBF_4$, $LiN(SO_2CF_3)_2$ or $LiN(SO_2C_2F_5)_2$ is from 70/30 to 99/1.

8. The nonaqueous electrolytic solution for lithium battery according to claim 1, wherein the compound of formula (I) is at least one selected from the group consisting of 1,2-ethanediol-2,4,5-trifluoro-3-methoxybenzoate methanesulfonate, 1,2-ethanediol-2,3,4,5,6-pentafluorobenzoate methanesulfonate, 2 butene-1,4-diol formate methanesulfonate, 2 butyne-1,4-diol formate methanesulfonate, and 2-butyne-1,4-diol-2,4,5-trifluoro-3-methoxybenzoate methanesulfonate.

9. A lithium secondary battery comprising a positive electrode, a negative electrode and a nonaqueous electrolytic solution of an electrolyte salt dissolved in a nonaqueous solvent, wherein the nonaqueous electrolytic solution comprises from 0.01 to 10% by mass of the nonaqueous electrolytic solution of at least one selected from the group consisting of 1,2-ethanediol acetate methanesulfonate, 1,3-propanediol acetate methanesulfonate, 1,4-butanediol acetate methanesulfonate, 2-butene-1,4-diol acetate methanesulfonate and a compound of formula (I):

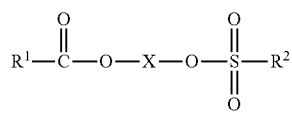
(I)

wherein
X is an alkylene group having from 1 to 6 carbon atoms, an alkenylene group having from 4 to 8 carbon atoms, or an alkynylene group having from 4 to 8 carbon atoms;
$R^1$ is a hydrogen atom, or a group of formula (II);
$R^2$ is an alkyl group having from 1 to 6 carbon atoms, a cycloalkyl group having from 3 to 8 carbon atoms, or a group of formula (II); with the proviso that at least one hydrogen atom of the alkyl group is optionally substituted with a halogen atom;

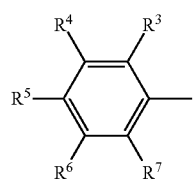
(II)

wherein $R^3$ to $R^7$ are each independently a hydrogen atom, a fluorine atom, a methoxy group, or an ethoxy group.

10. The lithium secondary battery according to claim 9, wherein the positive electrode comprises as an active material, a complex metal oxide of lithium containing cobalt, manganese or nickel, or a lithium-containing olivine-type phosphate.

11. The lithium secondary battery according to claim 9, wherein the negative electrode comprises as an active material, a carbon material having a graphite-type crystal structure.

12. A formyloxy group-containing compound of formula (III):

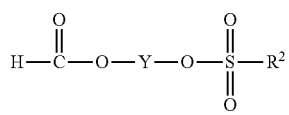
(III)

wherein

Y is an alkenylene group having from 4 to 8 carbon atoms, or an alkynylene group having from 4 to 8 carbon atoms; and $R^2$ is an alkyl group having from 1 to 6 carbon atoms, a cycloalkyl group having from 3 to 8 carbon atoms, or a group of formula (II); with the proviso that at least one hydrogen atom of the alkyl group is optionally substituted with a halogen atom;

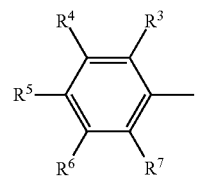
(II)

wherein $R^3$ to $R^7$ are each independently a hydrogen atom, a fluorine atom, a methoxy group, or an ethoxy group.

13. The nonaqueous electrolytic solution for a lithium battery according to claim 1, wherein
$R^2$ is a linear alkyl group having 1 to 6 carbon atoms, a linear alkyl group having 1 to 6 carbon atoms substituted with a halogen atom, a phenyl group or a phenyl group substituted only with at least one fluorine atom.

14. The nonaqueous electrolytic solution for a lithium battery according to claim 1, wherein
$R^2$ is a methyl group, an ethyl group or a trifluoromethyl group.

* * * * *

UNITED STATES PATENT AND TRADEMARK OFFICE
CERTIFICATE OF CORRECTION

PATENT NO.       : 8,383,274 B2                                                                Page 1 of 1
APPLICATION NO. : 13/003920
DATED            : February 26, 2013
INVENTOR(S)      : Koji Abe It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 113 days.

Signed and Sealed this
First Day of September, 2015

Michelle K. Lee
*Director of the United States Patent and Trademark Office*